US00PP37206P3

(12) United States Plant Patent
Olesen

(10) Patent No.: US PP37,206 P3
(45) Date of Patent: Jan. 13, 2026

(54) ROSE PLANT NAMED 'Poulpah111'

(50) Latin Name: *Rosa hybrida*
Varietal Denomination: Poulpah111

(71) Applicant: Mogens Nyegaard Olesen, Fredensborg (DK)

(72) Inventor: Mogens Nyegaard Olesen, Fredensborg (DK)

(73) Assignee: POULSER ROSER A/S, Fredensborg (DK)

( * ) Notice: Subject to any disclaimer, the term of this patent is extended or adjusted under 35 U.S.C. 154(b) by 99 days.

(21) Appl. No.: 17/803,616

(22) Filed: Sep. 13, 2022

(65) Prior Publication Data

US 2023/0210029 P1 Jun. 29, 2023

(30) Foreign Application Priority Data

Sep. 24, 2021 (QZ) ..... PBR 2021/2363

(51) Int. Cl.
*A01H 5/02* (2018.01)
*A01H 6/74* (2018.01)

(52) U.S. Cl.
USPC ..... Plt./117
CPC ..... *A01H 6/749* (2018.05)

(58) Field of Classification Search
USPC ..... Plt./117, 124, 118, 125
CPC ..... A01H 5/0222
See application file for complete search history.

(56) References Cited

PUBLICATIONS https://www.poulsenroser.dk/it/Roses/ShowProduct/82922; Jan. 9, 2024; 1 page.*
https://www.poulsenroser.dk/en/Roses/ShowProduct/82922; Jan. 9, 2024; 1 page.*
CPVO Application Consultation Version 4.12.33 for 'Poulpah111'; Jan. 9, 2024; 2 pages.*

* cited by examiner

*Primary Examiner* — Kent L Bell

(57) ABSTRACT

A new garden rose plant of the Miniature class which has abundant, white flowers and attractive foliage. This new and distinct variety has shown to be uniform and stable in the resulting generations from asexual propagation.

1 Drawing Sheet

Botanical designation: *Rosa hybrida.*
Variety denomination: 'Poulpah111'.

This application claims priority to Plant Breeder's Rights Application Number 2021/2363, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2016 and the resulting seeds were planted in a controlled environment in Fredensborg, Denmark. The new variety, named 'Poulpah111', originated as a single seedling from the stated cross.

The new variety may be distinguished from its male pollen parent and female seed parent primarily by the following characteristics. The male pollen parent plant has flowers generally toned RHS White Group 155A, while the new variety has white flowers with additional tonality of Yellow Group 8D. The female seed parent plant has orange-yellow flowers, while the newly claimed plant has white flowers with tones of yellow.

The objective of the hybridization of this rose variety was to create a new and distinct variety with unique qualities, such as:

1. Uniform and abundant white flowers;
2. Vigorous, but compact growth when propagated on its own roots;
3. Exceptional disease resistance; and
4. Production in containers.

This combination of qualities is not present in previously available commercial cultivars of this type, known to the inventor, and distinguish 'Poulpah111' from all other varieties of which we are aware.

As part of the rose development program, Mogens N. Olesen germinated the seeds from the aforementioned hybridization during winter of 2016 and conducted evaluations on the resulting seedlings in a controlled environment in Fredensborg, Denmark. 'Poulpah111' was selected in the spring of 2017 by the inventor as a single plant from the progeny of the aforementioned hybridization.

Asexual reproduction of 'Poulpah111' by rooted cuttings was first done by Mogens N. Olesen in the nursery in Fredensborg, Denmark in July 2017. This initial and other subsequent asexual propagations conducted in controlled environments have demonstrated that the characteristics of 'Poulpah111' are true to type and are transmitted from one generation to the next.

'Poulpah111', having demonstrated it's merits, Pulsen Roser A/S obtained the claimed plant directly from the Inventor for commercial applications.

DESCRIPTION OF THE DRAWING

The accompanying color illustration shows as true as is reasonably possible to obtain in color photographs of this type, the typical characteristics of the buds, flowers, leaves, and stems, of 'Poulpah111'.

Specifically illustrated in the drawing is an open flower viewed from above, petals detached, bare stem, partially open flower viewed from the side, sepals detached, receptacle, pedicel, reproductive flower parts, and leaves. Plants shown are 2 years of age.

DETAILED DESCRIPTION OF THE VARIETY

The following is a description of 'Poulpah111', as observed in its growth in a glass house located in Odense Denmark. Observed plants are 6 months of age, and were grown on their own roots in 24 cm containers. Color references are made using The Royal Horticultural Society (London, England) Colour Chart, 2001, except where common terms of color are used.

For a comparison, several physical characteristics of the rose variety 'Poulpah085', U.S. Plant Pat. No. 29,633 are compared to 'Poulpah111'. The claimed plant has a flower general tonality that is initially Yellow Group 8D becoming White Group 155B after flowers have fully matured. The comparison variety's tonality is White Group 155B. The flower diameter of 'Poulpah111' is 90 mm, while the comparison variety is 70 mm. The flower petal count for the claimed plant is 60, while the comparison is 45.

Flower And Flower Bud

Blooming habit: Continuous.

Flower bud: Size: Upon opening, 25 mm in length from base of receptacle to end of bud. Bud diameter is 12 mm. Bud form — Ovoid. Bud color — As sepals divide petals are Yellow-Green Group 145B and Green-White Group 157D. Sepal inner surface color Yellow-Green Group 147A. Texture — Lightly pubescent. Sepal outer surface color — Yellow-Green Group 146B. Texture — Smooth.

Sepal shape.—Apex: Typically subulate on two of the five sepals. Three of the five sepals are linear with foliaceous appendages. Base: Flat at union with receptacle. Sepal Margin — Margins have strong foliaceous appendages on three of the five sepals. Sepal size: 42 mm long, 10 mm wide.

Receptacle: Texture — Smooth. Receptacle size: 6 mm in height, 7 mm wide. Receptacle color: Yellow-Green Group 144A. Shape: Funnel. Pedicel: surface texture Smooth. Length: 60 mm. Diameter: 3 mm on average. Color: Yellow-Green Group 144A. Strength: Strong.

Flower bud development: Flower buds are borne single.

Flower bloom: Fragrance: Moderate, fresh floral scent. Duration: The blooms have a duration on the plant of approximately 21 days. Petals fall cleanly away from plant after flowers have fully matured. Size: Flower diameter is 90 mm when open. Flower depth is 45 mm. Flower shape: High centered, very double, with a high pointed center which is tightly closed. Shape of flower, side view: The upper portion is flat convex, while the lower portions is flat concave.

Petalage: Under normal conditions, flowers have about 60 petals.

General tonality of flower: Open flowers are initially Yellow Group 8D. White Group 155B after flowers have fully matured.

Petal color: Upon opening, outer petals Upper surface: Yellow Group 8D. Lower surface: Yellow Group 8D. Upon opening, inner petals: Upper surface: Yellow Group 11C. Lower surface: Yellow Group 11C. After opening, outer petals Upper surface: White Group 155B. Lower surface: White Group 155B with light intonations of Yellow-Green Group 145B. After opening, inner petals: Upper surface: White Group 155B with light intonations of Yellow-White Group 158C. Lower surface: White Group 155B.

Petals: Petal Reflex — Bilateral, strong. Margin: Entire and uniform. A small point at the center of the apex. Shape: Broad and elliptic. Apex shape: Rounded. Base shape: Acute. Petal Size: 43 mm (l)×55 mm (w). Texture: Smooth. Thickness: Average.

Petaloids: Size: 20 mm (l) by 15 mm (w). Quantity: About 8. Shape: Elliptical with an acute base and rounded or acute apex. Color: Yellow White Group 158C above and underneath. At the basal point of attachment, Yellow Group 4B.

Reproductive flower parts: Pollen: None observed. Anthers: Size: 2 mm in length. Color: Yellow Group 11C. Quantity: 65 on average. Filaments: Color: Yellow Group 7C. Length: 6 mm. Pistils: Length: 10 mm. Quantity: 24 on average. Stigmas: Color: White Group 155A. Styles: Color: Yellow-Green Group 145B.

Location of stigmas: Even in location relative to the length of the filaments and the height of the anthers. Hips: None Observed. 'Poulpah111' is susceptible to insect pests that normally affect the *Rosa* genus.

Plant

Plant growth: Upright. Plants are 73 cm in height, and 30 cm wide.

Stems: Color of juvenile growth: Yellow-Green Group 144B. Color of mature growth: Yellow-Green Group 144A. Length: Canes are about 20 to 50 cm from the base of the plant to the flowering portion. Diameter: About 6 mm. Internodes: On mature canes about 30 to 40 mm between nodes. Surface Texture: Young wood: Smooth. Older wood: Smooth. Prickles: None observed.

Plant foliage: Compound leaf dimensions: 140 mm (l)×110 (w). Quantity: 2 or 3 leaves per 10 cm of stem on average. Leaf bearing angle to the stem: 45 degrees. Color of juvenile foliage: Upper side: Yellow-Green Group 144A. Lower side: Yellow-Green Group 144B. Color of mature foliage: Upper side: Yellow-Green Group 146A. Lower side: Yellow-Green Group 147B.

Plant leaves and leaflets: Stipules: Size: 20 mm long, 2 to 3 mm wide. Quantity: 2 per compound leaf. Shape: Linear, slightly broad based with outward extending apices. Margins: Finely serrated. Color: Yellow-Green Group 144A. Petiole: Length: 18 mm. Diameter: 2 mm. Upper surface color: Anthocyanin Greyed-Purple Group 183B. Lower surface color: Yellow-Green Group 144A.

Rachis: Length: 40 mm. Upper surface color: Greyed-Purple Group 183B. Lower surface color: Yellow-Green Group 144A. Leaflet: Quantity: Normally 5 leaflets. Margins: Serrated. Size: Terminal leaflets are about 64 mm long, 46 mm wide. Shape: Generally elliptical. Base: Rounded.

Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah111' substantially as described and illustrated herein.

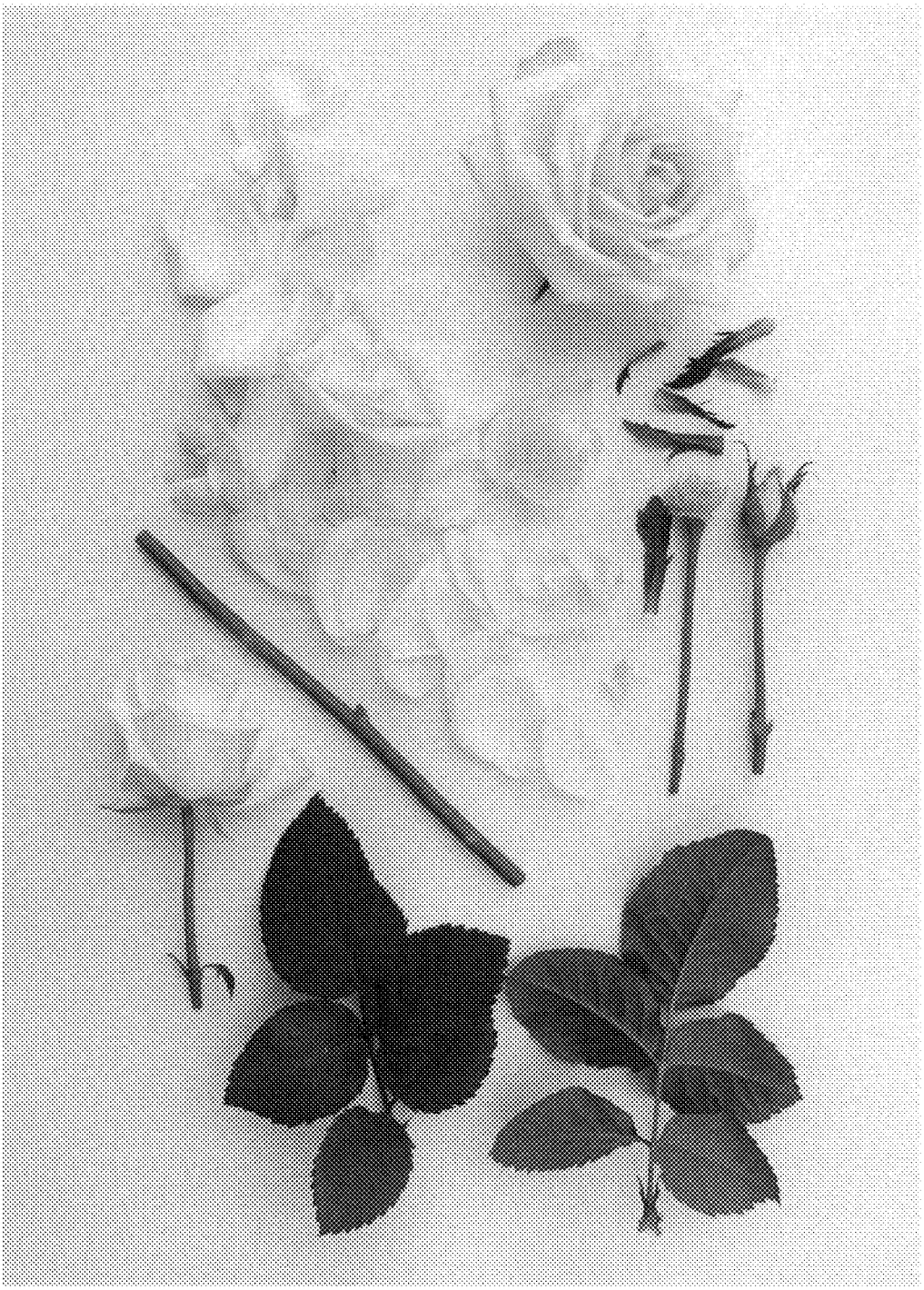

* * * * *